United States Patent [19]
Bethge et al.

[11] 4,430,509
[45] Feb. 7, 1984

[54] PROCESS FOR THE SEPARATION OF THE RACEMATE (R,S)-CYSTEINE

[75] Inventors: Horst Bethge, Hanau; Karlheinz Drauz, Freigericht; Axel Kleemann, Hanau; Jürgen Martens, Alzenau; Horst Weigel, Rodenbach, all of Fed. Rep. of Germany

[73] Assignee: Degussa Aktiengesellschaft, Frankfurt, Fed. Rep. of Germany

[21] Appl. No.: 460,858

[22] Filed: Jan. 25, 1983

[30] Foreign Application Priority Data

Jan. 26, 1982 [DE] Fed. Rep. of Germany ....... 3202295

[51] Int. Cl.$^3$ ............................................. C07B 19/00
[52] U.S. Cl. .................................. 562/401; 548/201; 562/557
[58] Field of Search ............................... 562/401, 557

[56] References Cited

U.S. PATENT DOCUMENTS 3,808,268 4/1974 Bambacher et al. ................ 562/401

OTHER PUBLICATIONS

Angewandte Chemie, vol. 93, p. 680, (and English Translation), Aug. 1981.

*Primary Examiner*—Natalie Trousof
*Assistant Examiner*—Vera C. Clarke
*Attorney, Agent, or Firm*—Cushman, Darby & Cushman

[57] ABSTRACT

To separate the racemate (R,S)-cysteine, the racemate is condensed in an inert solvent with an enantiomerically enantiomeric monosaccharide of the group of aldoses having 4 to 7 carbon atoms to form the corresponding 2-substituted thiazolidin-4-carboxylic acid and the mixture of diastereomers obtained separated from each other. Subsequently, the isolated unitary diastereomers are reacted in an inert solvent with a carbonyl reagent to split the ring and the enantiomerically pure cysteine in each case is isolated as such or as the corresponding cystine.

22 Claims, No Drawings

PROCESS FOR THE SEPARATION OF THE RACEMATE (R,S)-CYSTEINE

BACKGROUND OF THE INVENTION

The invention is directed to a process for the separation of racemic (R,S)-cysteine.

(R)-cysteine as well as its antipode (S)-cysteine has significance as an intermediate product for the production of pharmaceuticals or cosmetics and in peptide chemistry.

Since (R,S)-cysteine recently is accessible readily on an industrial scale (see Angew. Chem. Vol. 93, page 680 (1981)), there now is a particular need for a simple, economical, and efficient process for the separation of the racemate, (R,S)-cysteine.

SUMMARY OF THE INVENTION

The process of the invention is characterized by condensing (R,S)-cysteine in water, an alcohol, or ether having up to 5 carbon atoms and miscible with water or a mixture of such solvents with a pure enantiomeric monosaccharide of the general formula

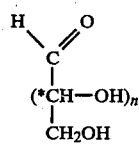  (I).

in which n is a whole number of 2 to 5 and *C indicates an asymmetrical carbon atom whereby the absolute configuration of the asymmetrical carbon atoms is the same or different, to form a 2-substituted thiazolidin-4-carboxylic acid of the general formula

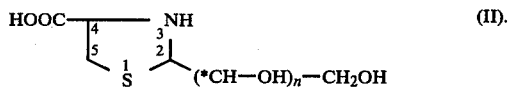  (II).

in which n and *C are as defined above, separating the mixture of diastereomers from each other, reacting the isolated, unitary diastereomer in water, an alcohol, or ether having up to 5 carbon atoms and miscible with water or a mixture of such solvents with a compound to split the ring, said compound containing the group —NH$_2$ and being capable of condensation with carbonyl groups, and isolating the pure enantiomeric cysteine obtained in each case, either as such or as the corresponding cystine.

As pure enantiomeric monosaccharides of general formula (I), for the condensation with the (R,S)-cysteine there are suited, for example, known aldoses such as L-arabinose, D-arabinose, L-galactose, D-galactose, L-glucose, D-glucose, L-mannose, D-mannose, L-xylose, D-xylose, D-ribose, L-ribose, D-threose, L-threose, D-lyxose, L-lyxose, D-erythrose, L-erythrose, D-gluco-α-heptose, L-gluco-α-heptose, D-manno-α-heptose, L-manno-α-heptose, D-allose, L-allose, D-talose, L-talose, D-idose, L-idose, D-gulose, or L-gulose.

The condensation is carried out in water or a water miscible alcohol or ether having up to 5 carbon atoms, for example methanol, ethanol, propan-1-ol, propan-2-ol, butan-1-ol, butan-2-ol, isobutanol, tert. butanol, pentan-1-ol, tetrahydrofuran or 1,4-dioxane or in a mixture of such solvents. The preferred solvents are water, methanol, or ethanol.

The pure enantiomeric monosaccharide of general formula (I) is suitably employed in an amount between 1 and 2.5 moles per mole of (R,S)-cysteine employed. However, it is especially advantageous to employ the monosaccharide and the (R,S)-cysteine in equimolar amounts. The order of addition is not critical.

The condensation suitably takes place at a temperature between 0° C. and the reflux temperature of the reaction mixture, preferably at a temperature between 20° and 70° C.

If instead of the free (R,S)-cysteine there is employed an acid addition salt of the same, e.g., the hydrochloride, then it is necessary before the condensation to bind the acid contained through addition of 1 to 1.5 equivalents of a base, especially of a tertiary amine such as triethylamine or pyridine.

In the condensation there is formed the corresponding 2-substituted thiazolidin-4-carboxylic acid of the general formula (II) in the form of a mixture of two stereoisomers, which are diastereomers and differ through the configuration in the 4 position of the thiazolidine ring. The two diastereomers can be separated from each other by fractional crystallization or by chromatographic methods.

There is obtained in the separation, in a given case after one or more recrystallizations from one of the solvents or solvent mixtures mentioned above for the condensation reaction, the sterically unitary compounds of general formula II, of which one exhibits in the 4-position the R-configuration and the other the S-configuration.

Frequently one or both diastereomers of general formula (II) already crystallizes out in the hot after the end of the condensation reaction. However, generally it is advantageous to hold the reaction mixture for a prolonged time at a temperature between 0° and 40° C. and, in a given case, insofar as the condensation was carried out in water, to add one of the above-mentioned solvents, e.g., an alcohol or ether.

The precipitated crystallizate is separated from the mother liquor through filtration or centrifugation. Generally, it consists completely or greatly predominantly of one of the two diastereomers of general formula (II). In case it is necessary, it can be further purified through recrystallization.

The mother liquor normally still contains a residual portion of the diastereomers separated off, but the other diastereomer is greatly enriched in the mother liquor. It can be brought to crystallization by concentration of the mother liquor, prolonged standing at lower temperature, addition of an organic solvent or by the combination of several of these procedures. Generally, it is then in lesser purity than the first diastereomer separated off. Therefore, an additional purification by recrystallization in many cases is likely to be suitable.

Alternatively, the two diastereomers of general formula (II) obtained as a mixture in the condensation can be separated through customary preparative chromatographic methods. Thereby, there takes place very substantial separation, and both of the diastereomers can be isolated in high purity.

The isolated, sterically unitary compounds of general formula (II) are now separately reacted in one of the solvents or mixture of solvents mentioned above for the condensation reaction with a compound for splitting the thiazolidine ring, which compound contains an amino group capable of condensing with the carbonyl group of the originally employed aldose.

There are suited for splitting the ring compounds; therefore, the typical carbonyl reagents such as hydroxylamine, e.g., in the form of the hydrochloride, hydrazine, e.g., in the form of the hydrate, phenylhydrazine, aniline or substituted anilines as o-, m-, or p-toluidine. They are employed in an amount at least equivalent to the amount of the compound of general formula (II) employed, but they can also be used in excess.

The ring splitting (fission of the ring) suitably is carried out at a temperature between 50° C. and the reflux temperature of the reaction mixture. It proceeds particularly quickly and completely if the reaction mixture is heated for about 0.5 to about 5 hours under reflux.

In the ring splitting, there is obtained from the diastereomers of general formula (II) having the R-configuration in the 4-position of the thiaolidine ring enantiomerically pure (R)-cysteine, from the diastereomers having the S-configuration in the 4-position the corresponding enantiomerically pure (S)-cysteine.

To separate the pure enantiomer of cysteine formed in the splitting of the ring from the simultaneously formed condensation product of the aldose employed and the carbonyl reagent used for splitting the ring, insofar as this condensation product is more difficulty soluble than the cysteine, first the condensation product is filtered off. Then the cysteine is isolated in crystalline form from the filtrate by concentration and/or adjustment of the pH to a value in the vicinity of the isoelectric point.

On the contrary, if the condensation product of the aldose employed and the carbonyl reagent used for the splitting of the ring is more readily soluble than the cysteine, then this is precipitated by adjustment of the pH to a value near the isoelectric point and separated.

Because of the lower solubility of cystine in comparison to that of cysteine, it can be more advantageous in many cases not to isolate as such the enantiomerically pure (R)-cysteine or (S)-cysteine formed in the splitting of the ring but instead to oxidize it with a suitable oxidation agent, for example, hydrogen peroxide to form (R,R)-cystine or (S,S-cystine) and to isolate this. The enantiomerically pure cystine then can be again easily reduced in known manner on demand to form the corresponding cysteine.

However, it is just as well also possible, after the end of the splitting of the ring, first to recover the main amount of the enantiomerically pure cysteine formed and subsequently to oxidize the residual portion remaining in the mother liquor to the corresponding cystine and to isolate it as such.

The process can comprise, consist essentially of, or consist of the steps recited with the stated materials.

The invention will be explained in further detail through the following examples. Unless otherwise indicated, all percentages are by weight.

DETAILED DESCRIPTION

Example 1

87.5 grams (0.5 mole) of (R,S)-cysteine×HCl×H$_2$O and 90 grams (0.5 mole) of D-(+)-galactose were boiled under reflux for 20 minutes in 3.75 liters of methyl alcohol, 50 ml of pyridine, and 50 ml of water. Within 2.25 hours, the reaction solution was slowly cooled to 40° C. and the crystals which separated out were filtered off with suction. After washing with methyl alcohol, there were obtained 40.5 grams of colorless crystals of (4S)-2-(D-galacto-1,2,3,4,5-pentahydroxypentyl)-thiazolidin-4-carboxylic acid, corresponding to a yield of 57.2% of theory.

$[\alpha]_D^{20} = +89.3°$ (c=0.5, H$_2$O).

By recrystallization from aqueous ethanol, the rotary value increased to +91.3°.

The rotary value of an authentic comparison sample produced from pure enantiomeric (S)-cysteine and D-(+)-galactose likewise was +91.3°.

Melting point: 178° with decomposition.

| Elemental analysis: C$_9$H$_{17}$NO$_7$S | % C | % H | % N |
|---|---|---|---|
| Found: | 39.25 | 5.93 | 4.79 |
| Calculated: | 39.14 | 6.04 | 4.94 |

There separated out of the filtrate after standing for three days a voluminous precipitate. After filtering off with suction, washing with methyl alcohol and drying, there were obtained 61.5 grams of colorless crystals in which the (4R)-2-(D-galacto)-1,2,3,4,5-pentahydroxypentyl)-thiazolidin-4-carboxylic acid is greatly enriched. By extraction with warm methyl alcohol, it can be isolated in pure form.

$[\alpha]_D^{20} = 71.2°$ (c=0.5, water). Melting point: 147° to 149° C.

By recrystallization from aqueous ethanol the rotary value increased to −78.2°.

The rotary value of an authentic comparison sample produced from pure enantiomeric (R)-cysteine and D-(+)-galactose likewise is −78.2°.

40.5 grams (0.145 mole) of (4S)-2-(D-galacto-1,2,3,4,5-pentahydroxypentyl)-thiazolidin-4-carboxylic acid and 13.3 grams (0.185 mole) of hydroxylamine hydrochloride were stirred with 700 ml of methyl alcohol and heated to boiling under reflux. After 20 minutes, a clear solution is formed. After 2 hours, the reaction is complete. The reaction solution is cooled off and freed from the oxime by filtration. The filtrate was adjusted to pH 6 with triethylamine, whereby 12.7 grams of (S)-cysteine crystallized out. (Yield: 72.7% of theory).

$[\alpha]_D^{20} = -9.5°$ (c=8, 1 N HCl).

40.5 grams (0.145 mole) of (4S)-2-(D-galacto-1,2,3,4,5-pentahydroxypentyl)-thiazolidin-4-carboxylic acid and 13.3 grams (0.185 mole) of hydroxylamine hydrochloride were stirred with 600 ml of methyl alcohol and heated to boiling under reflux. After 20 minutes, a clear solution is formed. After 3 hours, the reaction is complete. The reaction solution is cooled off and freed from the oxime by filtration. The filtrate was adjusted to pH 5.5 with triethylamine, whereby 12.7 grams of (R)-cysteine crystallized out. (Yield: 72.7% of theory).

$[\alpha]_D^{20} = +9.8°$ (c=8, 1 N HCl).

EXAMPLE 2

Alternatively, 7.1 grams (0.025 mole) of the (4S)-2-(D-galacto-1,2,3,4,5-pentahydroxypentyl)-thiazolidin-4-carboxylic acid obtained in Example 1 were made into a paste with 20 ml of water and stirred with 5.2 grams of a 24% aqueous hydrazine hydrate solution. The mixture was heated at 60° C. for 10 minutes. After cooling to room temperature, there were added dropwise 1.8 grams of 30% hydrogen peroxide, whereby (S,S)-cystine crystallized out immediately.

After filtering off with suction, washing with water, and drying, there were obtained 2.8 grams of pure (S,S)-cystine, corresponding to a yield of 93.3% of theory.

$[\alpha]_D^{20} = +218.7°$ (c=1, 1 N HCl).

EXAMPLE 3

17.5 grams (0.1 mole) of (R,S)-cysteine×HCl×H$_2$O and 18 grams (0.1 mole) of D-(+)-mannose were suspended in 300 ml of methyl alcohol and after the addition of 10 ml of pyridine were boiled under reflux for 1 hour. The product began to crystallize during the boiling. After cooling to 60° C., the product was filtered off with suction and washed with methyl alcohol. There were obtained 9.4 grams (66.4% of theory) of (4R)-2-(D-manno-1,2,3,4,5-pentahydroxypentyl)-thiazolidin-4-carboxylic acid as colorless crystals. $[\alpha]_D^{20} = -63.4°$ (c=0.5, water). By recrystallization from aqueous ethanol, the rotary value increased to −63.8°.

The rotary value of an authentic comparison sample produced from enantiomerically pure cysteine and D-(+)-mannose likewise is −63.8°.

Melting point: 177° C. with decomposition.

| Elemental analysis: C$_9$H$_{17}$NO$_7$S | % C | % H | % N |
|---|---|---|---|
| Found: | 39.02 | 6.08 | 4.88 |
| Calculated: | 39.14 | 6.04 | 4.94 |

The filtrate was cooled to 20° C. Thereby, there separated out a mixture of the two diastereomers, which was separated off and discarded. To the filtrate remaining, there was then added ethyl acetate as long as crystals separated out. By recrystallization from ethyl alcohol, there were obtained 4.7 grams (33.2% of theory) of (4S)-2-(D-manno-1,2,3,4,5-pentahydroxypentyl)-thiazolidin-4-carboxylic acid in pure form.

$[\alpha]_D^{20} = +100.5°$ (c=0.5, water).

The rotary value of an authentic comparison sample produced from enantiomerically pure (S)-cysteine and D-(+)-mannose is 101.1°.

Melting point: 153° C. (with decomposition).

9.4 grams (0.033 mole) of (4R)-2-(D-manno-1,2,3,4,5-pentahydroxypentyl)-thiazolidin-4-carboxylic acid and 6.88 grams (0.033 mole) of a 24% aqueous hydrazine hydrate solution were boiled with 95 ml of methyl alcohol for 30 minutes under reflux. The suspension obtained was filtered hot and the residue washed with hot 95% methyl alcohol. There were obtained 2.78 grams of (R)-cysteine (69.4% of theory).

$[\alpha]_D^{25} = +9.7°$ (c=8, 1 N HCl).

After diluting the filtrate with 70 ml of water and addition of 1.5 ml of 30% hydrogen peroxide, 2.2 grams of (R,R)-cystine crystallized out (26,6% of theory, based on the (4R)-2-(D-manno-1,2,3,4,5-pentahydroxypentyl)-thiazolidin-4-carboxylic acid employed).

$[\alpha]_D^{25} = -217°$ (c=1, 1 N HCl).

| Elemental analysis: C$_6$H$_{12}$O$_4$N$_2$S$_2$ | % C | % H | % N | % S |
|---|---|---|---|---|
| Found: | 29.98 | 5.07 | 11.82 | 26.63 |
| Calculated: | 29.99 | 5.03 | 11.66 | 26.69 |

4.7 grams (0.00165 mole) of (4S)-2-(D-manno-1,2,3,4,5-pentahydroxypentyl)-thiazolidin-4-carboxylic acid and 3.44 grams (0.00165 mole) of a 24% aqueous hydrazine hydrate solution were boiled with 50 ml of methanol for 45 minutes under reflux. The suspension obtained was filtered hot and the residue washed with hot 95% methanol. There were obtained 1.5 grams of (S)-cysteine, corresponding to a yield of 74.9% of theory.

$[\alpha]_D^{25} = -9.7°$ (c=8, 1 N HCl).

EXAMPLE 4

35 grams (0.2 mole) of (R,S)-cysteine×HCl×H$_2$O, 39.6 grams (0.2 mole) of D-(+)-glucose×H$_2$O and 20.2 grams (0.2 mole) of triethylamine were dissolved in 80 ml of water and 20 ml of methyl alcohol at 60° C. The solution was allowed to stand for 20 hours at room temperature. The crystals formed were filtered off and washed with methyl alcohol.

There were obtained 5.1 grams (36.0% of theory) of (4R)-2-(D-gluco-1,2,3,4,5-pentahydroxypentyl)thiazolidin-4-carboxylic acid. $[\alpha]_D^{20} = -84.6°$ (c=0.5, water). By recrystallization from aqueous ethanol, the rotary value increased to −89.6°.

The rotary value of an authentic comparison sample produced from enantiomerically pure (R)-cysteine and D-(+)-glucose likewise was −89.6°.

Melting point: 162° C. with decomposition.

| Elemental analysis: C$_9$H$_{17}$NO$_7$S | % C | % H | % N |
|---|---|---|---|
| Found: | 39.20 | 6.02 | 4.83 |
| Calculated: | 39.14 | 6.04 | 4.94 |

The filtrate resulting from the separation off of the (4R)-2-(D-gluco-1,2,3,4,5-pentahydroxypentyl)-thiazolidin-4-carboxylic acid was concentrated to 90 ml under reduced pressure. After standing overnight at 15° C., the mixture of (4R)- and (4S)-2-(D-gluco-1,2,3,4,5-pentahydroxypentyl)-thiazolidin-4 carboxylic acid crystallizing out was filtered off with suction. The filtrate resulting thereby was concentrated on the rotary evaporator at 25 mbar and concentrated to dryness by heating with a water bath. The residue was recrystallized from water. There was obtained pure (4S)-2-(D-gluco-1,2,3,4,5-pentahydroxypentyl)-thiazolidin-4-carboxylic acid in the form of colorless crystals. Yield: 4.8 grams (34% of theory).

Melting point: 168° C. with decomposition.

$[\alpha]_D^{20} = +85.1°$ (c=0.5, water).

The rotary value of an authentic comparison sample produced from enantiomerically pure (S)-cysteine and D-(+)-glucose is +85.2°.

5.1 grams (0.018 mole) of (4R)-2-(D-gluco-1,2,3,4,5-pentahydroxypentyl)-thiazolidin-4-carboxylic acid and 1.87 grams (0.027 mole) of hydroxylamine hydrochloride were heated under reflux to boiling in a mixture of 10 ml of water and 40 ml of methyl alcohol for 3.5 hours. After cooling a slight turbidity was removed by filtration and the filtrate was adjusted to pH 6 with triethylamine, whereby 1.62 grams of (R)-cysteine crystallized out (corresponding to a yield of 74.3% of theory).

$[\alpha]_D^{25} = +9.8°$ (c=8, 1 N HCl).

4.8 grams (0.017 mole) of (4S)-2-(D-gluco-1,2,3,4,5-pentahydroxypentyl)-thiazolidine-4-carboxylic acid and 1.87 grams (0.027 mole) of hydroxylamine hydrochloride were boiled under reflux for 4 hours in a mixture of 10 ml of water and 40 ml of methanol. After cooling to 20° C., a turbidity was removed by filtration and the filtrate adjusted to pH 5.5 with triethylamine, whereby 1.6 grams (79% of theory) of (S)-cysteine crystallized out.

$[\alpha]_D^{25} = -9.7°$ (c=8, 1 N HCl).

EXAMPLE 5

1.2 grams (0.01 mole) of (R,S)-cysteine and 1.5 grams (0.01 mole) of L-(+)-arabinose in 5 ml of water were heated at 80° C. for 30 minutes. The reaction solution obtained was separated by thin layer chromatography [silica gel 60 (E. Merck, Darmstadt), 2 mm thick layer], whereby as the mobile phase there was employed a mixture of 5 parts by volume of n-butanol, 2 parts by volume of ethanol, and 4 parts by volume of water. The pair of diastereomers was thus separated (Rf=0.17 and 0.29).

The zone at Rf=0.17 was separated from the DC plate and the (4R)-2-(L-arabino-1,2,3,4-tetrahydroxybutyl)-thiazolidin-4-carboxylic acid obtained therefrom by extraction with water, subsequent filtering off of the silica gel and concentrating to dryness. The residue was recrystallized from aqueous ethanol and consisted of (4R)-2-(L-arabino-1,2,3,4-tetrahydroxybutyl)-thiazolidin-4-carboxylic acid.

Melting point: 161° C.

The thus obtained product was heated under reflux at boiling for 3.5 hours with 0.52 gram (0.0075 mole) of hydroxylamine hydrochloride in a mixture of 5 ml of water and 15 ml of methanol. After cooling to 20° C., the turbidity was removed by filtration and the filtrate adjusted to pH 6 with triethylamine, whereby 0.4 grams of (R)-cysteine crystallized out (67% of theory).

$[\alpha]_D^{20} = +9.3°$ (c=12, 2 N HCl).

The zone at Rf=0.29 was separated from the DC-plate and extracted with water. The silica gel was filtered off, and the filtrate concentrated to dryness. In order to determine the melting point, a small part of the residue was recrystallized from aqueous ethanol.

Melting point: 164° C.

The thus obtained (4S)-2-(L-arabino-1,2,3,4-tetrahydroxybutyl)-thiazolidin-4-carboxylic acid was boiled at reflux for 3.5 hours with 0.52 grams (0.0075) of hydroxylamine hydrochloride in a mixture of 4 ml of water and 10 ml of methanol. The product was allowed to cool, filtered through two fluted filters, and the pH of the filtrate adjusted to 6. This took place through the addition of triethylamine. There crystallized out 0.36 gram, corresponding to 60% of theory of (S)-cysteine.

$[\alpha]_D^{20} = -9.4°$ (c=12, 2 N HCl).

The entire disclosure of German priority application P 3202295.6 is hereby incorporated by reference.

What is claimed is:

1. A process for the separation of the racemate (R,S)-cysteine comprising condensing the (R,S)-cysteine in a solvent which is water, a water miscible alcohol or ether having up to 5 carbon atoms or a mixture of such solvents with an enantiomerically pure monosaccharide of the formula

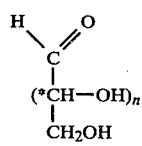

where n is a whole number from 2 to 5 inclusive and *C is an asymmetrical carbon atom to form a 2-position substituted thiazolidin-4-carboxylic acid of the formula

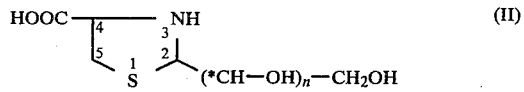

separating the diastereomers in the mixture obtained from each other and reacting the isolated diastereomer in a solvent which is water, a water miscible alcohol, or ether having up to 5 carbon atoms or a mixture of such solvents with a ring splitting compound containing the group —NH$_2$ and capable of condensing with a carbonyl group and isolating the enantiomerically pure cysteine obtained as such or as the corresponding cystine by oxidation.

2. A process according to claim 1 wherein the enantiomerically pure cysteine is isolated as such.

3. A process according to claim 1 including the steps of oxidizing the enantiomerically pure cysteine to form the corresponding cystine and isolating the cystine.

4. A process according to claim 1 wherein the monosaccharide has 5 to 6 carbon atoms.

5. A process according to claim 4 wherein the monosaccharide is galactose, glucose, mannose, arabinose, or xylose.

6. A process according to claim 5 wherein the monosaccharide is D-galactose, D-glucose, D-mannose, or D-arabinose.

7. A process according to claim 1 wherein the solvent employed is water, an alkanol having 1 to 5 carbon atoms or an ether which is, tetrahydrofuran or 1,4-dioxane, or a mixture of such solvents.

8. A process according to claim 1 wherein the condensation of the (R,S)-cysteine with the monosaccharide is carried out in water, methanol or ethanol, or a mixture of water and methanol or ethanol.

9. A process according to claim 5 wherein the condensation of the (R,S)-cysteine with the monosaccharide is carried out in water, methanol or ethanol, or a mixture of water and methanol or ethanol.

10. A process according to claim 8 wherein the condensation of the (R,S)-cysteine with the monosaccharide is carried out at a temperature between 20° and 70° C.

11. A process according to claim 1 wherein the condensation of the (R,S)-cysteine with the monosaccharide is carried out at a temperature between 20° and 70° C.

12. A process according to claim 11 wherein the ring splitting is carried out in water, methanol or ethanol, or a mixture of water and methanol or ethanol.

13. A process according to claim 10 wherein the ring splitting is carried out in water, methanol or ethanol, or a mixture of water and methanol or ethanol.

14. A process according to claim 8 wherein the ring splitting is carried out in water, methanol or ethanol, or a mixture of water and methanol or ethanol.

15. A process according to claim 1 wherein the ring splitting is carried out in water, methanol or ethanol, or a mixture of water and methanol or ethanol.

16. A process according to claim 15 wherein the ring splitting is obtained by heating the reaction mixture to the reflux temperature.

17. A process according to claim 14 wherein the ring splitting is obtained by heating the reaction mixture to the reflux temperature.

18. A process according to claim 13 wherein the ring splitting is obtained by heating the reaction mixture to the reflux temperature.

19. A process according to claim 10 wherein the ring splitting is obtained by heating the reaction mixture to the reflux temperature.

20. A process according to claim 8 wherein the ring splitting is obtained by heating the reaction mixture to the reflux temperature.

21. A process according to claim 1 wherein the ring splitting is obtained by heating the reaction mixture to the reflux temperature.

22. A process according to claim 1 wherein the compound containing the —$NH_2$ group is hydroxylamine, hydrazine, aniline, phenyl hydrazine, or a salt thereof.

* * * * *